United States Patent
Rios et al.

(10) Patent No.: US 12,324,853 B2
(45) Date of Patent: Jun. 10, 2025

(54) METHODS FOR TREATING RESPIRATORY VIRAL INFECTIONS

(71) Applicant: Quimica Luar S.R.L., Córdoba (AR)

(72) Inventors: Nicolas Martinez Rios, Córdoba (AR); Adrian Javier Muñoz, Córdoba (AR); Roxana Valeria Alasino, Quebrada de las Rosas (AR); Ariel Gustavo Garro, Barrio las Rosas (AR); Dante Miguel Beltramo, Barrio P. Capital (AR); Galia Kalayan, Córdoba (AR); Nestor Garcia, Córdoba (AR)

(73) Assignee: Quimica Luar S.R.L., Córdoba (AR)

( * ) Notice: Subject to any disclaimer, the term of this patent is extended or adjusted under 35 U.S.C. 154(b) by 51 days.

(21) Appl. No.: 17/397,820

(22) Filed: Aug. 9, 2021

(65) Prior Publication Data

US 2022/0040098 A1 Feb. 10, 2022

Related U.S. Application Data

(60) Provisional application No. 63/090,424, filed on Oct. 12, 2020, provisional application No. 63/063,541, filed on Aug. 10, 2020.

(51) Int. Cl.
| | | |
|---|---|---|
| A61K 9/00 | (2006.01) | |
| A61K 31/555 | (2006.01) | |
| A61K 47/02 | (2006.01) | |
| A61P 11/00 | (2006.01) | |

(52) U.S. Cl.
CPC .......... *A61K 9/0078* (2013.01); *A61K 31/555* (2013.01); *A61K 47/02* (2013.01); *A61P 11/00* (2018.01)

(58) Field of Classification Search
None
See application file for complete search history.

(56) References Cited

U.S. PATENT DOCUMENTS

| | | |
|---|---|---|
| 4,607,038 A | 8/1986 | Ogata et al. |
| 5,856,345 A | 1/1999 | Doi et al. |
| 5,885,597 A | 3/1999 | Botknecht et al. |
| 7,186,186 B2 | 3/2007 | Imahata |
| 7,186,417 B1 | 3/2007 | Siegel et al. |
| 7,452,523 B2 | 11/2008 | Hofmann et al. |
| 10,973,787 B2 * | 4/2021 | Argañarás ............... A61K 45/06 |
| 2008/0260863 A1 | 10/2008 | Warner et al. |
| 2012/0115897 A1 | 5/2012 | Tang et al. |
| 2013/0178448 A1 | 7/2013 | Caparros-Wanderley et al. |
| 2015/0105468 A1 | 4/2015 | Martinez-Alzamora et al. |
| 2020/0237689 A1* | 7/2020 | Peralta ................. A61K 47/186 |
| 2021/0275476 A1* | 9/2021 | Argañarás ................ A61K 9/08 |

FOREIGN PATENT DOCUMENTS

| | | |
|---|---|---|
| CN | 102138893 A | 8/2011 |
| WO | 2012/099479 A1 | 7/2012 |

OTHER PUBLICATIONS

Munoz et al. (Pharmaceuticals 2018, 11, 47 (2018)).*
Cox et al. (Lancet Microbe. 2020 (May11(1):e11).*
Elvers et al. (Letters in Applied Microbiology 1995, 20, 82-84).*
Sanyal et al. (Letters in Applied Microbiology 1993, 17, 1090111).*
Al-Janabi, In vitro antibacterial activity of Ibuprofen and acetaminophen. J Glob Infect Dis. May 2010;2(2):105-8.
Alasino et al., Characterization of the inhibition of enveloped virus infectivity by the cationic acrylate polymer eudragit E100. Macromol Biosci. Sep. 11, 2007;7(9-10):1132-8.
Archyde, Ibuprofen and coronovarus: "There is no logic in treating COVID-19 without an anti-inflammatory." Retrieved online at: https://www.archyde.com/ibuprofen-and-coronavirus-there-is-no-logic-in-treating-covid-19-without-an-anti-inflammatory/. 4 pages, Jun. 11, 2020.
Bernard et al., The effects of ibuprofen on the physiology and survival of patients with sepsis. The Ibuprofen in Sepsis Study Group. N Engl J Med. Mar. 27, 1997;336(13):912-8.
Bolivia Verifica, Nebulized ibuprofin is not certin to attack the coronavirus. Retrieved online at: https://boliviaverifica.bo/en/no-es-seguro-que-el-ibuprofeno-nebulizado-ataque-al-coronavirus/. 4 pages, Jun. 25, 2020.
Byrne et al., Aspirin and ibuprofen enhance pyrazinamide treatment of murine tuberculosis. J Antimicrob Chemother. Feb. 2007;59(2):313-6.
Celik et al., Effects of ibuprofen on the physiology and outcome of rabbit endotoxic shock. BMC Infect Dis. Oct. 31, 2002;2:26-38.
ClinicalTrials.gov, Inhaled Ibuprofen to Treat COVID-19 (CordobaTrial). ClinicalTrials.gov Identifier: NCT04382768, 8 pages, Jun. 11, 2020.
Diarios Bonaerenses, Nebulized ibuprofen found to inactivate Covid-19 and improve respiratory conditions. Retrieved online at: https://dib.com.ar/2020/05/descubren-que-el-ibuprofeno-nebulizado-inactiva-el-covid-19-y-mejora-los-cuadros-respiratorios/. 2 pages, May 7, 2020.
Garcia et al., Ibuprofen, a traditional drug that may impact the course of COVID-19 new effective formulation in nebulizable solution. Med Hypotheses. Nov. 2020;144:110079, 3 pages.
Graham et al., In vivo susceptibility of Campylobacter pylori. Am J Gastroenterol. Mar. 1989;84(3):233-8.
Guzman et al., Antitubercular specific activity of ibuprofen and the other 2-arylpropanoic acids using the HT-SPOTi whole-cell phenotypic assay. BMJ Open. Jun. 20, 2013;3(6):e002672.
Infobae, Ibuprofen and coronavirus: "It does not make sense to treat COVID-19 without an anti-inflammatory." Retrieved online at: https://www.infobae.com/america/tendencias-america/2020/06/11/ibuprofeno-y-coronavirus-no-tiene-logica-tratar-el-covid-19-sin-un-antiinflamatorio/. 3 pages, Jul. 11, 2020.

(Continued)

*Primary Examiner* — Patricia Duffy
*Assistant Examiner* — Garen Gotfredson
(74) *Attorney, Agent, or Firm* — McCarter & English, LLP; Steven G. Davis; Zhongyu Wang

(57) ABSTRACT

Disclosed is a method of treating a subject for a respiratory viral infection. The method comprises administering to the subject by inhalation an effective amount of a hypertonic saline solution comprising an ibuprofenate salt.

18 Claims, 7 Drawing Sheets

(56) References Cited

OTHER PUBLICATIONS

InfoGei, Argentine scientists discover that nebulized ibuprofen is beneficial for patients with COVID-19. Retrieved online at: https://infogei.com/nota/32037/cientificos-argentinos-descubren-que-el-ibuprofeno-nebulizado-es-beneficioso-para-pacientes-con-covid-19/. 2 pages, May 8, 2020.

Lanas et al., Estrategia clinica para el paciente que precisa antiinflamatorios no esteroides: posicion de los inhibidores de la COX-2. Gastroenterol Hepatol. 2001;24:22-36.

LaVoz, Coronavirus: details on how the therapy protocol works in Cordoba. Retrieved online at: https://www.lavoz.com.ar/ciudadanos/coronavirus-detallan-como-es-protocolo-de-terapia-cordobesa/. 4 pages, May 15, 2020.

Mohsen et al., Antibacterial, Anti-biofilm Activity of Some Non-steroidal Anti-Inflammatory Drugs and N-acetyl Cysteine against Some Biofilm Producing Uropathogens. American Journal of Epidemiology and Infectious Disease. 2015;3(1)1-19.

Onischuk et al., Analgesic effect from Ibuprofen nanoparticles inhaled by male mice. J Aerosol Med Pulm Drug Deliv. Sep. 2009;22(3):245-53.

Pagina 12, The innovative ibuprofen treatment that showed good results against coronavirus. Retrieved online at: https://www.pagina12.com.ar/264405-el-innovador-tratamiento-con-ibuprofeno-que-dio-buenos-resul. 2 pages, May 8, 2020.

Pina-Vas et al., Antifungal activity of ibuprofen alone and in combination with fluconazole against *Candida* species. J Med Microbiol. Sep. 2000;49(9):831-840.

Reed et al., A Simple Method of Estimating Fifty Per Cent Endpoints. Am J Hygiene. May 1938;27(3):493-497.

Ridell et al., Amphiphilic association of ibuprofen and two nonionic cellulose derivatives in aqueous solution. Journal of Pharmaceutal Sciences. 1999;88(11):1175-1181.

Sordelli et al., Ibuprofen modifies the inflammatory response of the murine lung to Pseudomonas aeruginosa. Eur J Respir Dis. Aug. 1985;67(2):118-27.

Telam, Scientists from Cordoba manage to reverse coronavirus cases using modified ibuprofen. Retrieved online at: https://www.telam.com.ar/notas/202005/460734-cientificos-cordoba-coronavirus.html. 4 pages, Jul. 5, 2020.

UniDiversidad, The innovative ibuprofen treatment that controls the coronavirus condition. Retrieved online at: https://www.unidiversidad.com.ar/el-innovador-tratamiento-con-ibuprofeno-que-dio-buenos-resultados-contra-el-covid-19. 3 pages, May 8, 2020.

\* cited by examiner

| Characteristics | Nebulized Ibuprofen (Argentina) In yet another embodiment, the concentration of ibuprofenate salt dissolved in the hypertonic saline solution is between 5 mM to 50 mM. | Remdesivir: Beigel (control) | Remdesivir: Beigel (active) | Denmark Population Survey | Hydroxy-chloroquine: Brazil (control arm | Dexamethasone Study: RECOVERY (usual care arm, O2 recipients) |
|---|---|---|---|---|---|---|
| Number of Patients | 30 | 522 | 541 | 689 | 227 | 2604 (57% were ≤ age70) |
| Mean Age-years | 51.4 | 59.2 | 58.6 | 70 | 49.9 | 66.4 |
| % male | 73 | 63.6 | 65.1 | 58.1 | 54.2 | 63 |
| % with no major risk factors | 53.0% | 22.5% | 19.5% | na | na | 43% |
| In-Hospital Mortality | 0 of 30 | 11.90% | 7.10% | 23.80% | 6/173 (3.5%) | 682/2604 (26.2%) (if < 70 years of age: 17%) |

FIG. 7

METHODS FOR TREATING RESPIRATORY VIRAL INFECTIONS

RELATED APPLICATION INFORMATION

This application claims priority to U.S. Provisional Application No. 63/063,541, filed Aug. 10, 2020; and to U.S. Provisional Application No. 63/090,424, filed Oct. 12, 2020, both of which are incorporated herein by reference.

BACKGROUND

Respiratory viruses (including coronavirus, influenza and the like) are highly transmissible human respiratory pathogens that cause seasonal, endemic infections as well as periodic, unpredictable pandemics. They are characterized by the sudden onset of high fever, cough, headache, fatigue, muscle weakness and pain, sore throat, and a runny or stuffy nose. These infections are highly contagious and predominantly transmitted through airborne respiratory secretions released when an infected individual coughs or sneezes.

Most patients with respiratory viral infections recover within a week without treatment. However, severe and even life threatening disease can develop in some cases. For example, the infection can affect the lungs and cause pneumonia, resulting in infection and hyperinflammation of the air sacs in the lungs accompanied with the build-up of fluid and inflammatory cells and severe breathing difficulties. Patients with these severe symptoms require hospitalization. In more severe cases, patients develop acute respiratory distress syndrome (ARDS), which involves a severe life threatening inflammatory cascade that inter alia diminishes the lungs' ability to provide vital organs with enough oxygen. As a consequence, low blood oxygen levels, i.e., hypoxia, are a defining characteristic of more severe disease. In the most severe cases, patients require ventilators to provide life sustaining levels of oxygen in their blood until hyperinflammation decreases or patient's progression to death. Mortality rates for patients with influenza viral pneumonia and ARDS that require ventilator assistance can be quite high, ranging up to 30% up to 70%. Similar outcomes have been observed as a consequence of COVID19, particularly in high-risk patients, as described below.

There is at the moment an urgent need for treatments against respiratory viruses, given the current coronavirus COVID 19 (SARS-CoV-2 virus) pandemic, and fears of future novel human or avian influenza pandemics. At the time of this writing, COVID 19 has caused over 210,00 deaths in the United States and over 1,070,000 deaths worldwide, and there are only two approved drugs with demonstrated efficacy in treating COVID 19 infection, remdesivir and dexamethasone. Remdesivir is an anti-viral, but has a number of shortcomings. Specifically, it is an intravenous drug and is therefore suitable only in a hospital setting. Although it can shorten recovery times (Beigel et al, *New England Journal of Medicine* May 22, 2020 DOI: 10.1056/NEJMoa2007764), it's greatest benefit may be observed in less critically ill patients. Dexamethasone is an anti-inflammatory corticosteroid that was shown in preliminary findings in the United Kingdom's national clinical trial RECOVERY to reduce mortality by one third for patients on ventilators and by one fifth for patients only on oxygen. See https://www.nature.com/articles/d41586-020-01824-5. While remdesivir and dexamethasone clearly provides some benefits, the considerable mortality rate among COVID 19 patients treated with remdesivir and dexamethasone points to the urgent need for more effective treatments or treatment combinations.

SUMMARY

It has now been found that critically ill patients infected with the coronavirus showed significant improvement after being administered a nebulized hypertonic sodium ibuprofenate solution by inhalation. Specifically, respiratory rates moved towards normal and oxygenation levels as measured by pulse oximetry improved dramatically early after initial treatment, with return to normal or near normal levels within about five to seven days in several severely hypoxic patients infected with COVID 19 (see e.g., FIGS. 5 and 6). This rapid and unexpected improvement in oxygenation is unlikely to result solely from an antiviral effect. Based on this surprising effect, methods of treating respiratory viral infections with the hypertonic sodium ibuprofenate solution are disclosed herein.

The invention is directed to a method of treating a subject for a respiratory viral infection. The method comprises administering to the subject by inhalation an effective amount of a hypertonic saline solution comprising an ibuprofenate salt.

Another embodiment of the invention is a hypertonic saline solution comprising an ibuprofenate salt for treating a respiratory viral infection in a subject by inhalation.

Another embodiment of the invention is the use of a hypertonic saline solution comprising an ibuprofenate salt for the manufacture of a medicament for treating a respiratory viral infection in a subject by inhalation.

BRIEF DESCRIPTION OF DRAWINGS

FIG. 7 is a table comparing the effectiveness of the treatment disclosed herein in COVID-19 patients against treatments in Major Clinical Trials.

DETAILED DESCRIPTION

Figure 1:
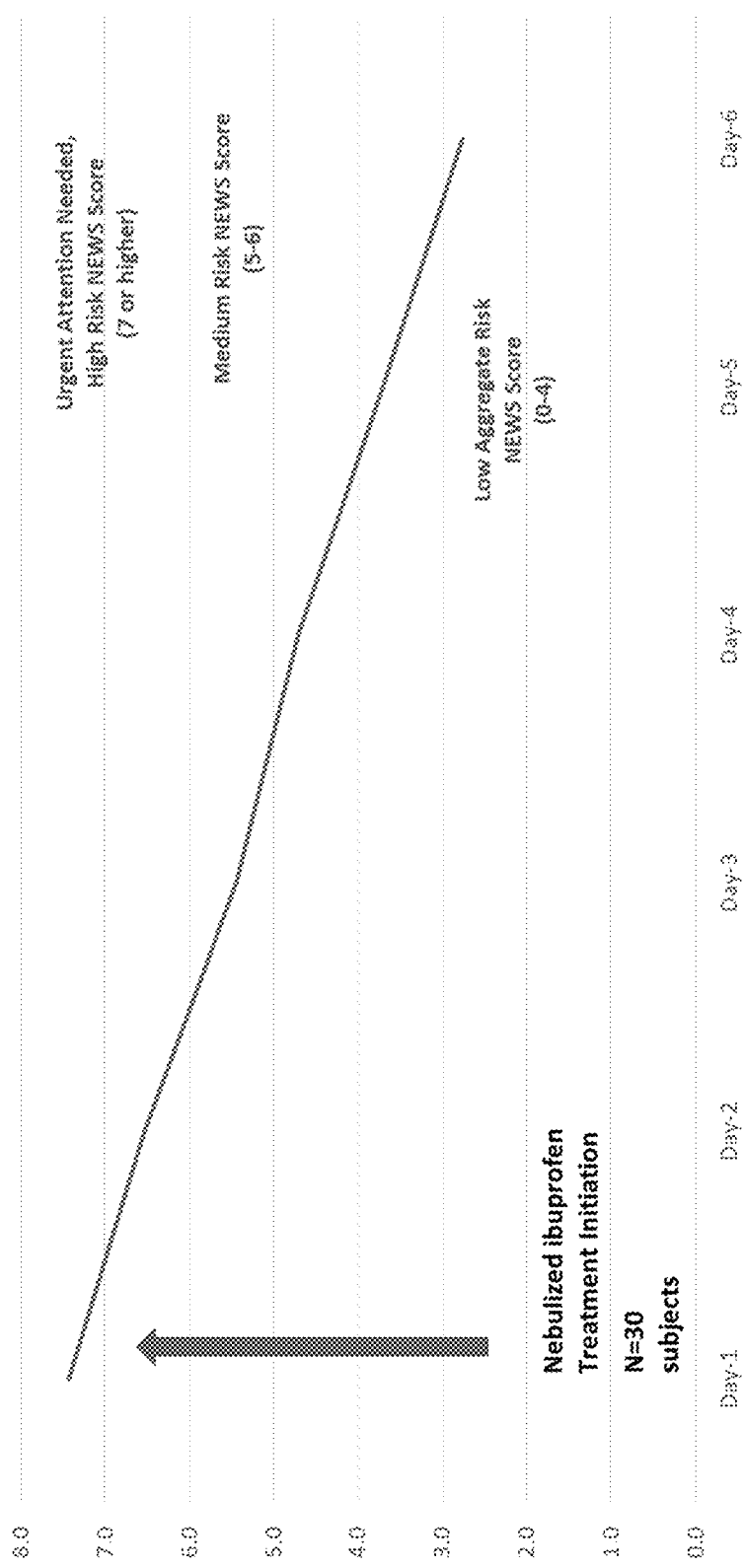
FIG. 1 illustrates the mean NEWS2 score, Pre-Dose Day 1 to Day 6, of the disclosed hypertonic sodium ibuprofenate solution in hospitalized patients with confirmed COVID-19 infection.

The present invention is directed to the use of salts of ibuprofen (i.e., "ibprofenate salts") in a hypertonic saline solution for the treatment of respiratory viral infections in a subject. Ibuprofen has the following chemical structure:

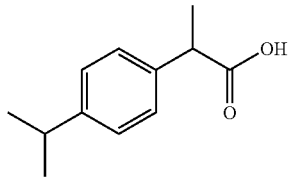

Given that ibuprofen has one chiral center, it has two possible enantiomers R and S. The invention contemplates the use of the R enantiomer, the use of the S enantiomer and mixtures thereof, including racemic mixtures (1:1 mixtures of the R and S enantiomers). The designation of the R enantiomer or the S enantiomer indicates an optical purity of at least 90%, 95%, 98% or 99% by weight. "Optical purity" refers to the percent of the designated enantiomer relative to the combined weight of both enantiomers.

"Ibuprofenate" refers to a deprotonated form of ibuprofen, i.e., wherein the carboxylic acid group is deprotonated. "Ibuprofenate salt" refers to a deprotonated form of ibuprofen in which the proton on the carboxylic acid group is replaced with another cation, e.g., a lithium, sodium or potassium cation to form lithium, sodium or potassium ibuprofenate. In one embodiment, the disclosed formulation comprises sodium ibuprofenate.

"Hypertonic saline" refers to an aqueous solution of sodium chloride in which the concentration of sodium chloride is greater than found in physiological saline (i.e., 0.9% w/v). In one embodiment, the hypertonic saline solution used in the disclosed methods comprises between 0.3 M to 2.0 M sodium chloride. Alternatively, the hypertonic saline solution used in the disclosed methods comprises between 0.5 M to 1.5 M sodium chloride. In another embodiment, the hypertonic saline solution used in the disclosed methods comprises between 0.5 M to 1.25 M sodium chloride. In yet another embodiment, the hypertonic saline solution used in the disclosed methods comprises between 0.8 M to 1.25 M sodium chloride. In yet another embodiment, the hypertonic saline solution used in the disclosed methods comprises 1.0 M sodium chloride. In another embodiment, the hypertonic saline solution used in the disclosed methods comprises between 0.3 M to 1.5 M sodium chloride. In another embodiment, the hypertonic saline solution used in the disclosed methods comprises between 0.3 M to 1.0 M sodium chloride. In another embodiment, the hypertonic saline solution used in the disclosed methods comprises between 0.3 M to 0.7 M sodium chloride. In another embodiment, the hypertonic saline solution used in the disclosed methods comprises 0.5 M sodium chloride. In yet another embodiment, the hypertonic saline solution comprises greater than 0.3 M sodium chloride. References to the concentration of sodium chloride in the hypertonic saline solution refers to the concentration of sodium chloride dissolved in the solution.

The hypertonic saline solution used in the disclosed methods comprises an ibuprofenate salt dissolved therein. In one embodiment, the concentration of ibuprofenate salt dissolved in the hypertonic saline solution is between 5 mM to 100 mM. In another embodiment, the concentration of ibuprofenate salt dissolved in the hypertonic saline solution is between 25 mM to 75 mM. In another embodiment, the concentration of ibuprofenate salt dissolved in the hypertonic saline solution is between 40 mM to 60 mM. In yet another embodiment, the concentration of ibuprofenate salt dissolved in the hypertonic saline solution is between 5 mM to 50 mM. In yet another embodiment, the concentration of ibuprofenate salt dissolved in the hypertonic saline solution is 50 mM.

The pH of the hypertonic saline solution used in the disclosed methods is between 7.0 and 9.0. Alternatively, the pH is between 7.0 and 8.0. In yet another alternative, the pH is between 7.5 and 7.9. In another alternative, the pH of the hypertonic saline solution is between 8.0 and 10.0. In another alternative, the pH of the hypertonic saline solution is between 8.0 and 9.0. In another alternative, the pH of the hypertonic saline solution is between 8.5 and 9.5. In another alternative, the pH of the hypertonic saline solution is between 8.5 and 9.0. In another alternative, the pH of the hypertonic saline solution is 8.5. In another embodiment, the pH of the hypertonic saline solution is 9.0.

A respiratory viral infection is a viral infection that affects the upper or lower respiratory tract. Examples of respiratory viral infections include Influenza A (e.g., the currently circulating human H1N1 and H3N2 strains, as well as avian flu strains such as H5N1, H7N9 and others which occasionally infect humans as well as 'swine flu' strains), Influenza B, Adenoviruses, Coronaviruses (e.g., SARS-CoV, SARS-CoV-2, MERS-CoV, 229E, NL63, OC43, and HKU1), Parainfluenza Viruses (e.g., Type 1, Type 2, Type 3 and Type 4), Respiratory Syncytial Virus strains (RSV), Human Rhinoviruses (multiple serotypes), and Human Metapneumoviruses. In one embodiment, the respiratory viral pathogen is SARS-CoV-2 (the COVID-19 virus). In another embodiment, the respiratory viral pathogen is Influenza A. In another embodiment, the respiratory viral pathogen is Influenza B. Symptoms of respiratory viruses generally include high fever, cough, headache, fatigue, muscle weakness and pain, sore throat, and a runny or stuffy nose. These symptoms are characteristic of "mild disease" and are referred to herein as "mild symptoms". In another embodiment, a specific diagnosis of viral pathogen is not established, but the subject has symptoms characteristic of a respiratory viral infection.

A small but significant percentage of subjects with a respiratory viral infection progress to severe and even life-threatening disease such as pneumonia or acute respiratory distress syndrome (ARDS) (referred to herein as "severe disease"). Pneumonia is an infection that inflames the air sacs (alveoli) in one or both lungs. The air sacs may fill with fluid or pus (purulent material), causing cough with phlegm or sputum, fever, chills, and difficulty breathing. ARDS is also characterized by fluid build-up in the air sacs in the lungs, but it is also accompanied by hyperinflammation, which may induce a condition sometimes referred to as "cytokine storm" or systemic inflammation which can lead to respiratory failure and death. Symptoms of ARDS include severe shortness of breath, labored and unusually rapid breathing, low blood pressure and/or confusion and extreme tiredness.

Low blood oxygenation levels also accompany pneumonia and ARDS and are responsible, at least in part, for the severe symptoms associated with these conditions. Oxygen saturation levels offer an integrated assessment of pulmonary and cardiac function, and its non-invasive measurement with transdermal pulse oximetry has become a routine component of the assessment of disease severity. "Low blood oxygenation levels" in a subject refers to a pulse-oximetry oxygen saturation level of less than 95%, the lower limit of normal for healthy subjects (patients with hypercapneic respiratory disease live with lower chronic oxygen saturation levels). Oxygen saturation of <92% is considered an urgent matter, requiring immediate intervention, particularly when this reflects an acute change from baseline normal values as is often observed in patients with viral pneumonitis. A subject with a low blood oxygenation level is also referred to herein as being "hypoxic". Subjects with respiratory viral infections who have progressed to pneumonia or ARDS, when treated according to the disclosed methods, have shown improved blood oxygenation, including restoration of blood oxygenation levels to normal and with relief of the severe symptoms associated with ARDS.

A second common measure of cardiopulmonary status is the respiratory rate, which in healthy adults is typically less than or equal to 20 breaths/minute. Subjects with respiratory viral infections that have progressed to pneumonia or ARDS frequently present with respiratory rates far in excess of the normal range (up to 21-25 breathes/minute, 25-30 breathes/minute or, in more severe cases, 30 to 40 breaths/minute), and such subjects, when treated according to the disclosed methods, have shown improvement in respiratory rate to the normal range. This is one component of the alleviation of severe symptoms associated with ARDS described above.

A third measure of cardiopulmonary status is the heart rate, which in healthy adults at rest is typically less than 90 beats per minute, but may be markedly elevated in subjects with respiratory viral infections that have progressed to pneumonia or ARDS. Subjects with respiratory viral infections that have progressed to pneumonia or ARDS frequently present with heart rates far in excess of normal range (from 91-110 beats/minute, in more severe cases from 111-130 beats/minute, to over 131 beats/minute in the most severe cases). Subjects with viral pneumonia or ARDS, when treated according to the disclosed methods, have shown improvement in heart rate to the normal range.

The National Early Warning Score (NEWS2) is an accepted assessment tool for identifying subjects who have or are likely to develop acute illness. See, for example, Royal College of Physicians, *National Early Warning Score (NEWS) 2: Standardizing the Assessment of Acute-Illness Severity in the NHS*. Updated Report of the Working Party, London:RCP, 2017. Specifically, a NEWS2 Score of 0-4 indicates a low level of clinical risk for the subject; a NEWS2 Score of 5-6 indicates a moderate level of clinical risk for the subject; and a NEWS2 Score of 7 or more indicates a high level of clinical risk for the subject. The disclosed methods can be used to treat a subject with a NEWS2 Score of 0-4, 5-6 or 7 or more to reduce the likelihood of increasing the scope or to reduce the score to bring the subject to an improved condition with a lower score.

In particularly severe cases, subjects with ARDS require breathing assistance and are put on a mechanical ventilator, i.e., the subject is "intubated". The disclosed methods can increase blood oxygenation and are useful in reducing the likelihood that a hypoxic subject with severe disease who is not yet intubated will subsequently require intubation. The disclosed methods are also useful in increasing blood oxygenation in intubated patients, thereby increasing the likelihood of recovery and decreasing the amount of the time the subject spends on a ventilator.

In some instances, subjects with respiratory viral infections who are experiencing only mild symptoms may nonetheless be hypoxic, i.e., have low blood-oxygen levels. The low blood oxygenation levels are an indication that the subject with only mild symptoms is at risk for progressing to severe disease, such as pneumonia or ARDS. The disclosed methods of treatment are effective in reducing the likelihood that hypoxic subjects experiencing only mild symptoms will progress to severe disease such as pneumonia or ARDS. As noted above, the disclosed methods of treatment have also been shown to be effective in treating subjects who are hypoxic and who have already developed more severe disease such as pneumonia or ARDS.

The disclosed methods can also be used to treat non-hypoxic subjects with respiratory viral infections who experiencing only mild symptoms to reduce the likelihood of these subject becoming hypoxic and/or progressing to severe disease. The disclosed methods can also be used to treat hypoxic subjects with respiratory viral infections who experiencing only mild symptoms to reduce the likelihood of these subject becoming hypoxic and/or progressing to severe disease.

It is well known that subjects with respiratory viral infections are at increased risk of developing severe disease if they have one, two or more risk factors for developing ARDS. Examples of underlying risk factors include, for example, diabetes, obesity (body mass index of 30 or higher), asthma, a compromised immune system, hypertension, atrial fibrillation, hypertension, heart failure and coronary artery disease, chronic obstructive pulmonary disease, emphysema, obstructive sleep apnoea syndrome, asthma, age above 65, cancer, immunosuppression, chronic kidney failure, chronic hepatitis, chronic liver failure or lung damage due to smoking. It is advantageous to treat a subject with a respiratory viral infection having one, two or more risk factors according to the disclosed methods while the subject is non-hypoxic, i.e., is still experiencing mild disease, to reduce the likelihood of progressing to more severe disease, e.g., to a hypoxic state and/or pneumonia or ARDS. It is also advantageous to treat a hypoxic subject with a respiratory viral infection who is experiencing only mild disease having one, two or more risk factors according to the disclosed methods to reduce the likelihood of progressing to more severe disease, e.g., to pneumonia or ARDS.

The hypertonic saline formulation used in the disclosed methods is administered by inhalation. Administering a formulation by "inhalation" refers to administering the formulation directly to the lungs through the mouth or/and nasal cavity, commonly by inhaling the formulation.

Administration of the hypertonic saline formulation can be accomplished by nebulization, in which a nebulizer changes liquid medicine into fine droplets (in aerosol or mist form) that are inhaled through a mouthpiece or mask. Nebulization can be accomplished by any suitable means, including by: 1) jet, which uses compressed gas to make an aerosol (tiny particles of medication in the air) or ultrasound, which makes an aerosol through high-frequency vibrations. In one embodiment, the nebulization is carried out with a piston nebulizer. In one embodiment, the nebulized droplets are of a sufficient size to reach the alveoli, e.g., less than 0.1 microns or less than 0.8 microns or less than 0.5 microns.

Alternatively, the hypertonic saline formulation may be delivered with an inhaler. In one example, the hypertonic saline formulation is administered through a metered dose inhalers (MDI), which "pushes out" a pre-measured spray of the hypertonic saline formulation, with, for example, a hydrofluoroalkane aerosol spray. In another example, a soft mist inhaler (SMI) provides a pre-measured amount of the hypertonic saline formulation in a slow-moving mist.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Treat," "treating," or "treatment," when used in connection with a subject with a respiratory viral infection, includes improving the effects or symptoms of infection or shortening the duration of the infection. In instances where the subject has become hypoxic, "treat," "treating," or "treatment," refers to returning blood oxygenation to normal or near normal more rapidly than in the absence of treatment. In instances where the subject has progressed to severe disease, "treat," "treating," or "treatment," refers to lessening the likelihood of requiring intubation, decreasing the time requiring intubation, decreasing recovery time and/or reducing mortality rate. A subject "at risk" of developing severe disease belongs to a subgroup of subjects known to more frequently progress to severe disease compared with subjects generally. Treatment is preferably administered before the progression to severe disease. Improvements in or lessening of the severity of a symptom of the respiratory viral infection and blood oxygenation levels can be readily assessed according to standard methods and techniques known in the art.

"Effective amount" means an amount when administered to the subject with a respiratory viral infection which results in beneficial or desired results, including improvement of the effects or symptoms of respiratory viral infection, including normalizing blood oxygenation levels, shortening recovery time, decreasing the likelihood of requiring intubation in severe disease and/or decreasing mortality.

The precise amount of the hypertonic saline solution administered to provide an "effective amount" to the subject will depend on the type, and severity of the respiratory viral infection, and on the characteristics of the subject, such as general health, age, sex, body weight, and tolerance to drugs. The skilled artisan will be able to determine appropriate dosages depending on these and other factors. Suitable dosages are known for approved therapeutic agents and can be adjusted by the skilled artisan according to the condition of the subject, the type of respiratory viral infection being treated and the amount of hypertonic saline solution being used by following, for example, dosages reported in the literature and recommended in the *Physician's Desk Reference* (57th ed., 2003). For example, an "effective amount" can be between 1 mL to 50 mL of the hypertonic saline solution used in the disclosed methods. Alternatively, an "effective amount" is between 1 mL to 25 mL of the hypertonic saline solution used in the disclosed methods. In another alternative, "effective amount" is between 1 mL and 10 mL of the hypertonic saline solution used in the disclosed methods. In another alternative, "effective amount" is between 3 mL and 7 mL of the hypertonic saline solution used in the disclosed methods. In yet another alternative, an "effective amount" is 5 mL of the hypertonic saline solution used in the disclosed methods. An effective amount is administered between 1 and 5 times daily, alternatively from 1 to 3 times daily. The time of administration varies between 5 minutes and 1 hour and alternatively between 5 minutes and 30 minutes. In yet another alternative, the time of administration varies between 10 minutes and 20 minutes.

The preparation of the hypertonic saline solution used in the disclosed methods is described in U.S. Published Application 2018/0296509, the entire teachings of which are disclosed herein by reference.

Exemplification

The following examples are intended to be illustrative and are not meant in any way to limit the scope of the disclosure. Compassionate-Use of Nebulized Na-Ibuprofenate for Treatment of COVID-19 Infection in Hospitalized Patients Hospitalized patients with confirmed COVID-19 infection and tachypnea/hypoxia were offered compassionate-use nebulized sodium-ibuprofenate in hypertonic saline by their treating physicians. Accepting patients were treated as follows:

50 mg of Na-ibuprofenate was administered per nebulization in 5 ml saline (0.5 M sodium chloride), without any dilution. Nebulization was performed three times per day at eight hour intervals. Nebulization occurred until oxygen supplementation was no longer required. This happened before day 14 of treatment. The nebulization was carried out using a self-designed hood that generates negative flux connecting the upper part to the hospital aspiration system, with a heat and moisture exchange filter (HMEF).

Data from 30 treated patients is provided below.

TABLE 1

National Early Warning Score (Version 2) Correlation to Physiological Parameters

| Physiological Parameter | Score | | | | | | |
|---|---|---|---|---|---|---|---|
| | 3* | 2 | 1 | 0 | 1 | 2 | 3* |
| Respiration rate (per min) | ≤8 | | 9-11 | 12-20 | | 21-24 | ≥25 |
| SpO$_2$ scale 1(%) | ≤91 | 92-93 | 94-95 | ≥96 | | | |
| SpO$_2$ scale 2 (%) | ≤83 | 84-85 | 86-87 | 88-92 ≥93 on air | 93-94 on oxygen | 95-96 on oxygen | ≥97 on oxygen |
| Air or oxygen? | | oxygen | | air | | | |
| Systolic blood pressure (mmHg) | ≤90 | 91-100 | 101-110 | 111-219 | | | ≥220 |
| Pulse (per minute) | ≤40 | | 41-50 | 51-90 | 91-110 | 111-130 | ≥131 |
| Consciousness | | | | Alert | | | CVPU |
| Temp (°C.) | ≤35.0 | | 35.1-36.0 | 36.1-38.0 | 38.1-39.0 | ≥39.1 | |

*Score of 3 connotes extreme physiologic disturbance

NEWS2 thresholds and triggers are discussed. An individual having a score of 3 in any individual parameter was classified as being of low-medium clinical risk.

TABLE 2

Baseline Characteristics of Patients

| Baseline Characteristic | Compassionate Use Nebulized Na-Ibuprofenate (N = 30) |
|---|---|
| Mean Age (years) | 51.4 |
| Male Patients (%) | 22 (73.3) |
| Any Risk Factor Identified (%) | 14 (47%) |
| Obesity (%) | 9 (30%) |
| Diabetes (%) | 4 (13%) |
| Cardiovascular disease (includes hypertension) (%) | 5 (17%) |
| Chronic lung disease (%) | 3 (10%) |
| Proportion Receiving Supplemental Oxygen at Day-1 Timepoint | 30 (100%) |
| Mean Baseline Oxygen Saturation (by Pulse Oximetry) | 89.1% |
| Mean Baseline Respiratory Rate (breathes/minute) | 29.7 |
| Mean Baseline NEWS2 Score | 7.4 Range: 1-11 Median: 8.0 |

Figure 2:
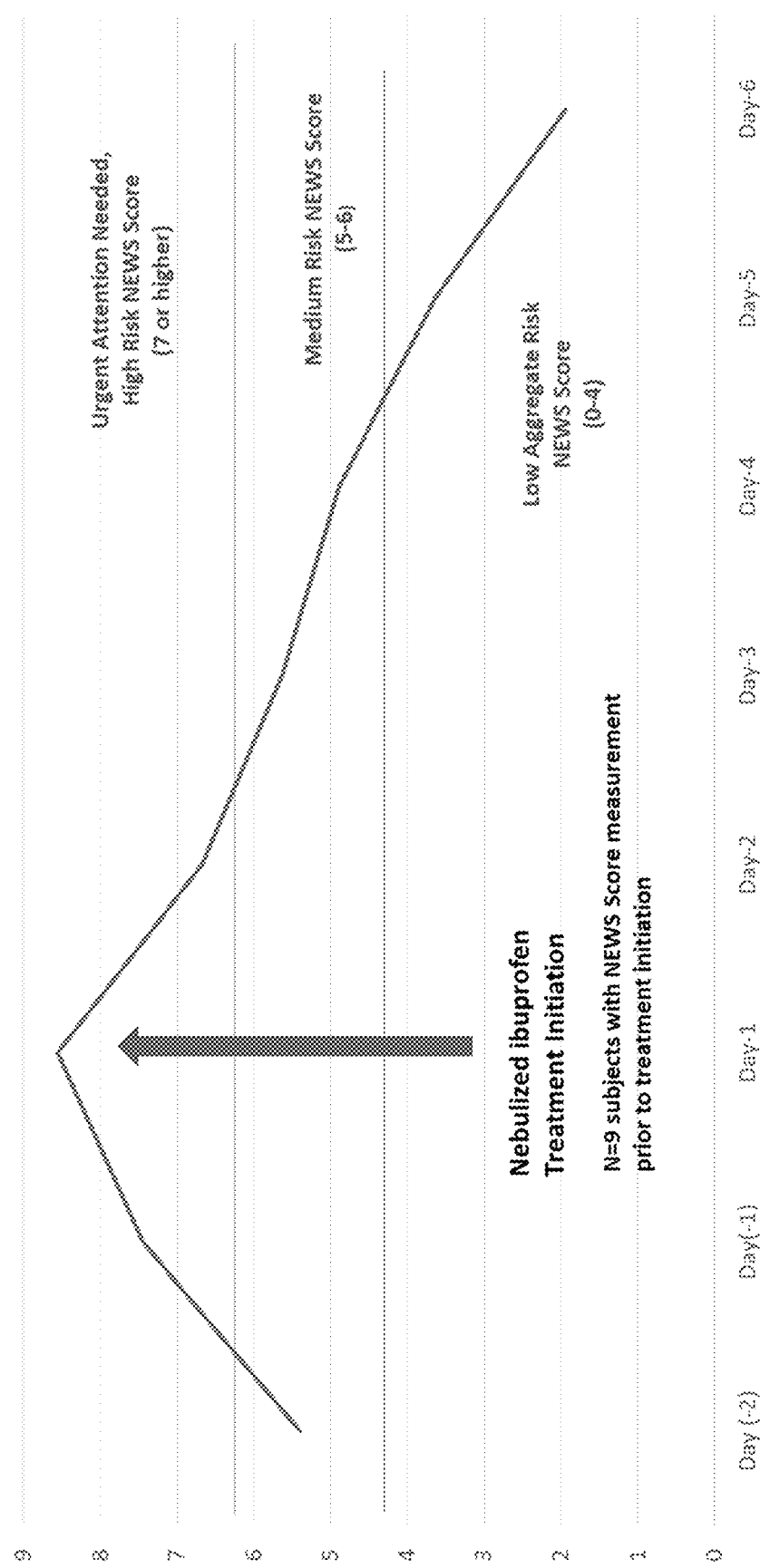
FIG. 2 illustrates the mean NEWS2 score: pre- and post-initiation of dosing of the disclosed hypertonic sodium ibuprofenate solution in hospitalized patients with confirmed COVID-19 infection.
Figure 3:
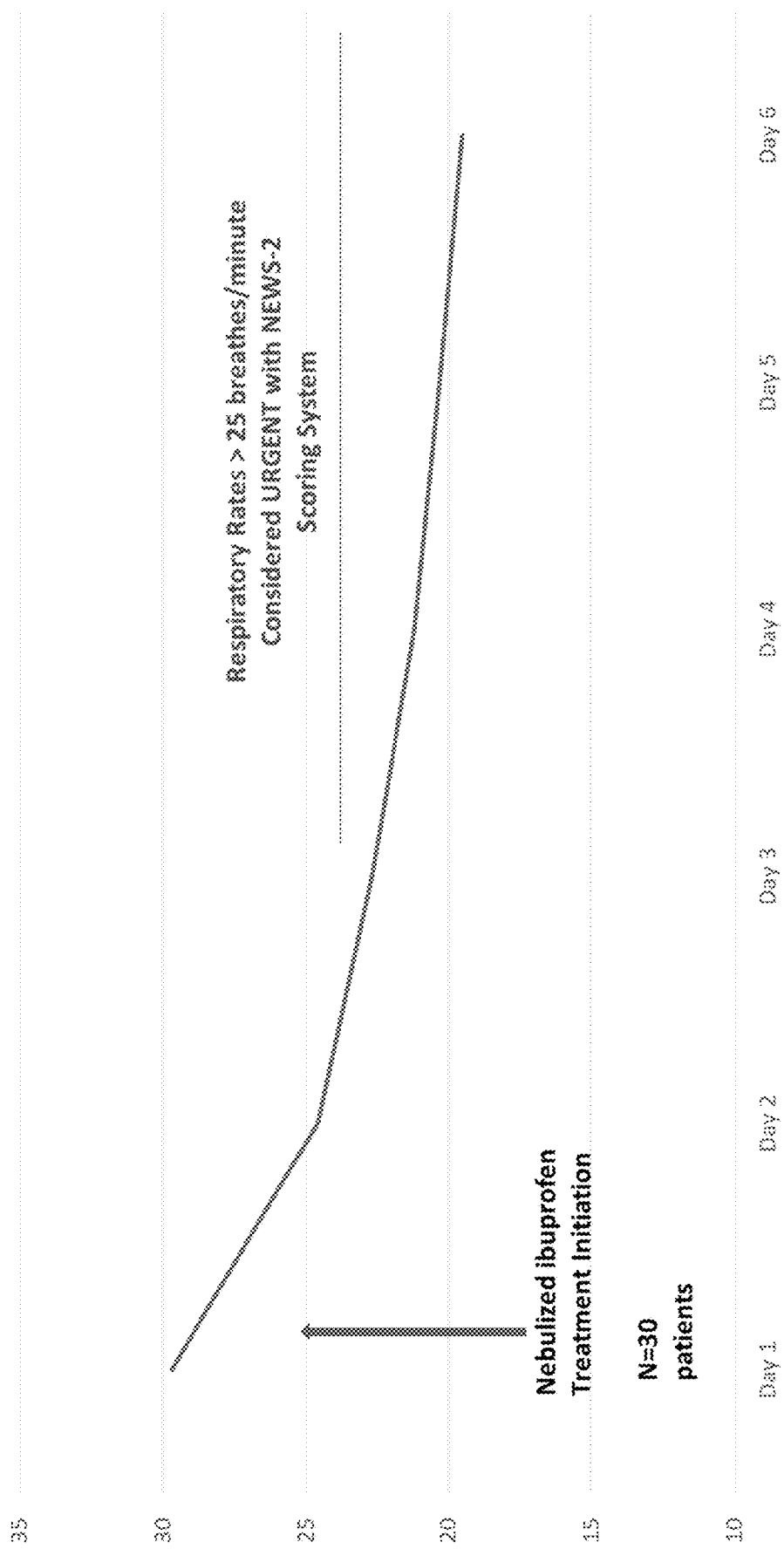
FIG. 3 illustrates the respiratory rate (bpm) following initiation of administration of the disclosed hypertonic sodium ibuprofenate solution in hospitalized patients with confirmed COVID-19 infection.
Figure 4:
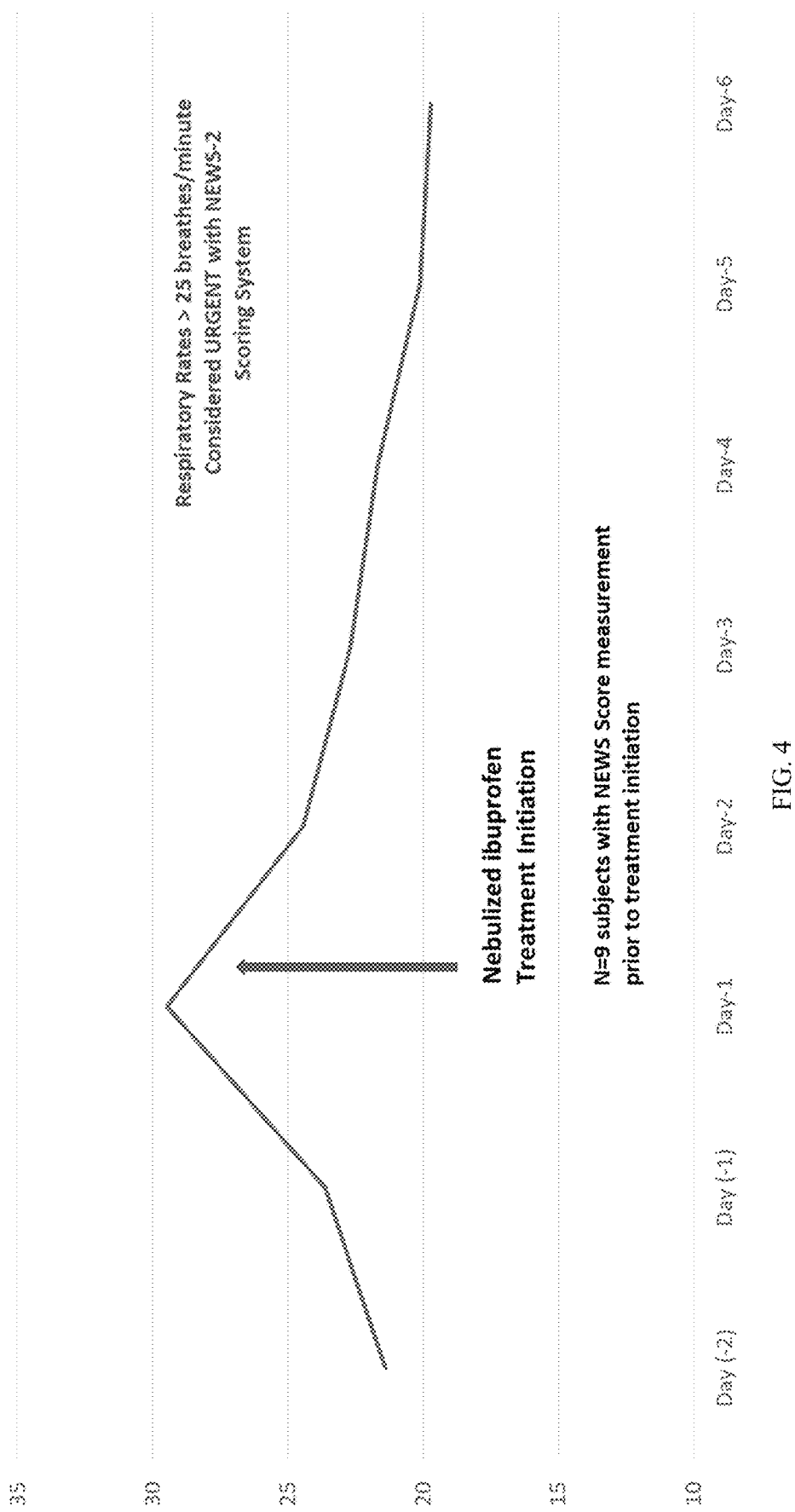
FIG. 4 illustrates the respiratory rate (bpm) pre-and-post initiation of administration of the disclosed hypertonic sodium ibuprofenate solution in hospitalized patients with confirmed COVID-19 infection.
Figure 5:
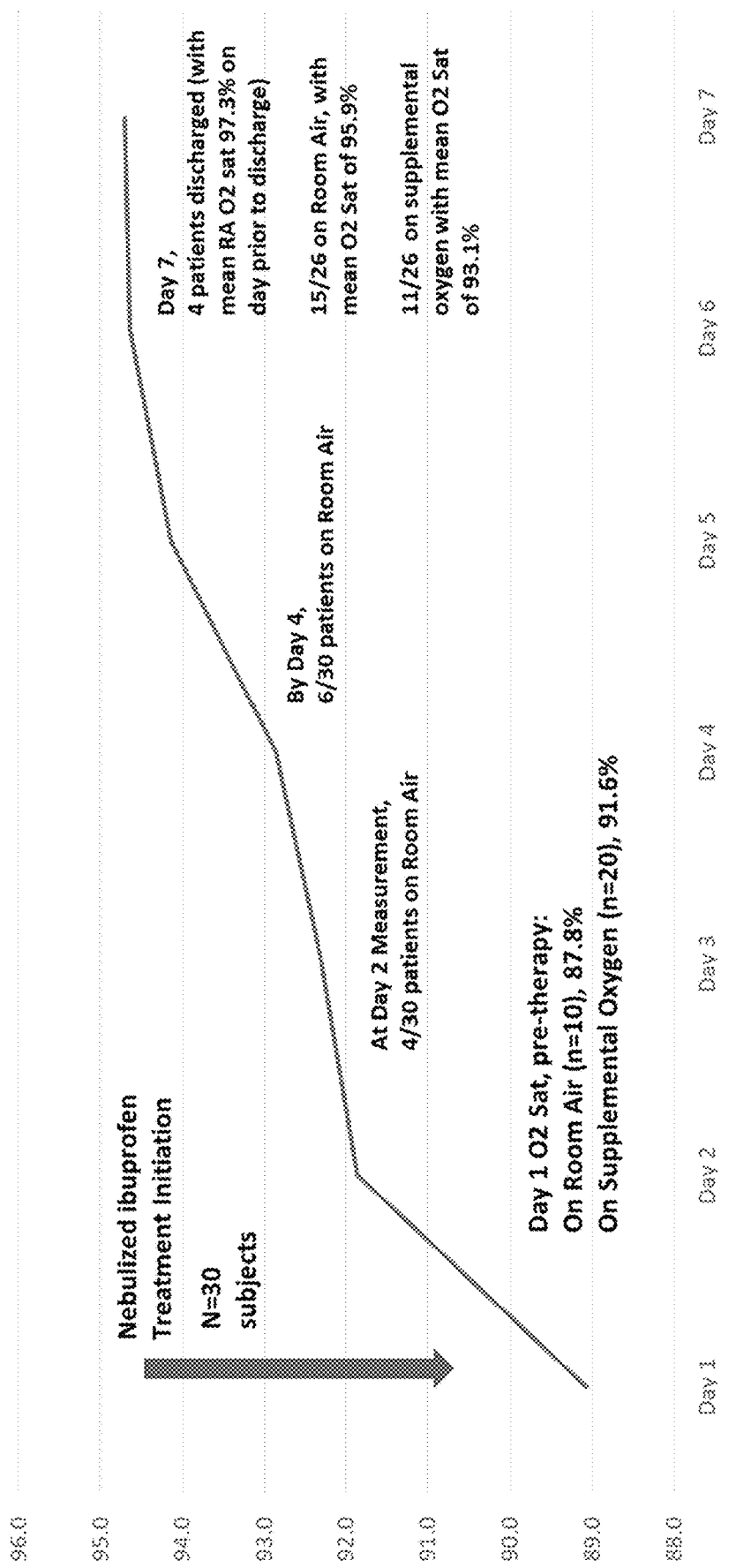
FIG. 5 illustrates the mean pulse oximetry oxygen saturation in hospitalized patients with confirmed COVID-19 infection and treated with the disclosed hypertonic sodium ibuprofenate solution in hospitalized patients with confirmed COVID-19 infection
Figure 6:
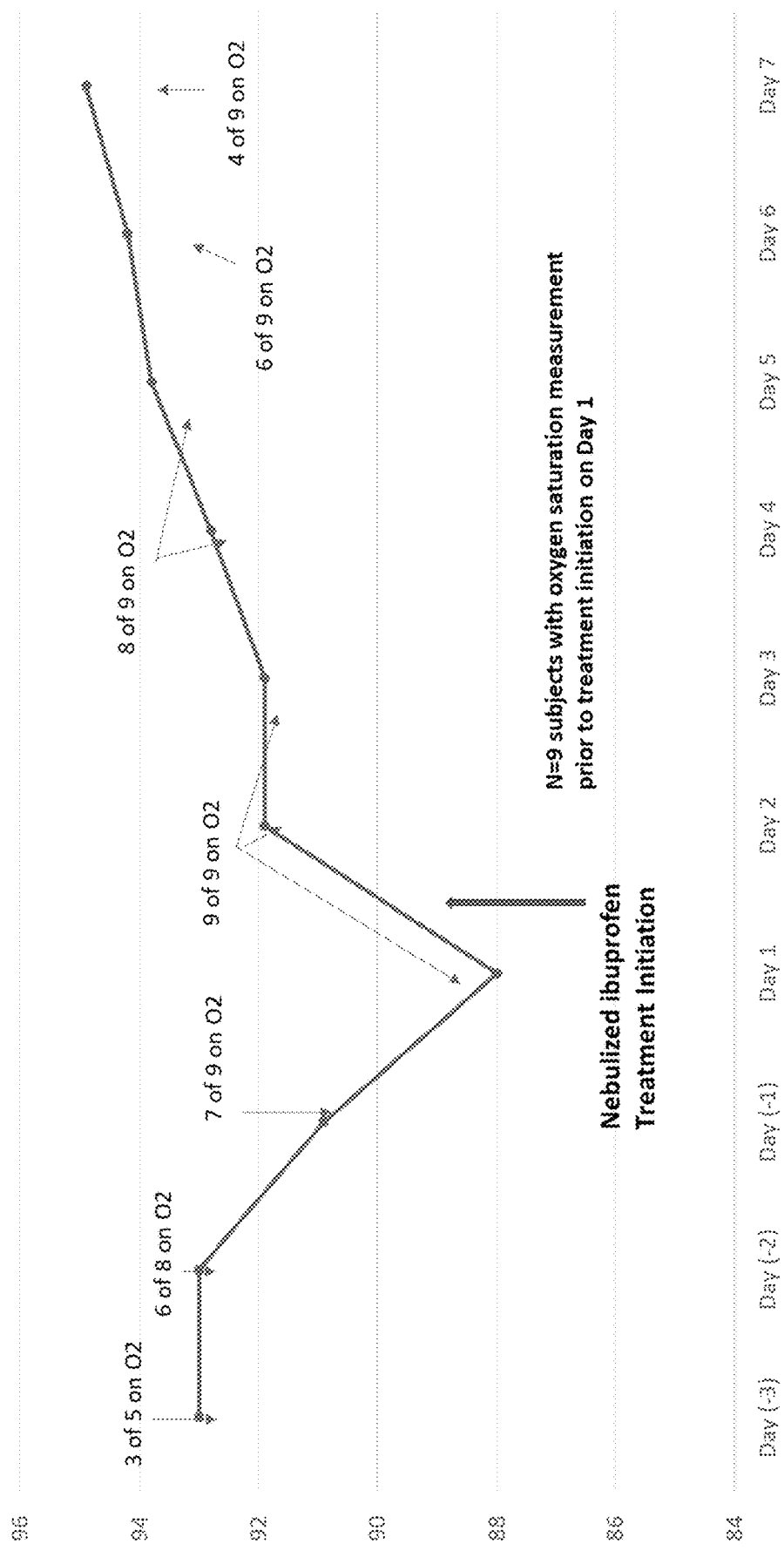
FIG. 6 illustrates the pulse oximetry % oxygen saturation, pre-and-post initiation administration of the disclosed hypertonic sodium ibuprofenate solution in hospitalized patients with confirmed COVID-19 infection.

Results are shown in FIGS. 1-6. Overall, there was severe disease in most patients treated as indicated by hypoxia, tachypnea and NEWS2 (28 of 30 with NEWS Score≥5, mean score 7.4 and median score 8.0). Yet, with treatment of the inventive solution, all 30 patients survived to hospital discharge or stability, and no patients progressed to need for mechanical ventilation. For patients with baseline-trend data prior to therapy, acute reversal in deteriorating physiologic parameters was observed. A steady improvement in multiple parameters was observed in all patient with clinicians reporting a dramatic improvement in patient well-being within 24 to 48 hours of therapy initiation.

What is claimed is:

1. A method of treating a subject for a respiratory SARS-COV-2 viral infection, comprising administering to the subject by inhalation an effective amount of an aqueous hypertonic saline solution comprising an ibuprofenate salt, wherein the subject is hypoxic and the hypertonic saline solution is administered until blood oxygenation levels of the subject return to normal; or wherein the subject has a respiratory rate of at least 21-25 breathes/minute and the hypertonic saline solution is administered until the respiratory rate of the subject has returned to normal.

2. The method of claim 1, wherein the ibuprofenate salt is the sodium, potassium or lithium salt of ibuprofenate.

3. The method of claim 1, wherein the ibuprofenate salt is the sodium salt of ibuprofenate.

4. The method of claim 3, wherein the concentration of the ibuprofenate salt in the hypertonic saline solution is from 5 mM to 100 mM.

5. The method of claim 4, wherein the concentration of NaCl in the hypertonic saline solution is from 0.3 M to 2.0 M.

6. The method of claim 5, wherein the concentration of NaCl in the hypertonic saline solution is from 0.3 M to 1.0 M.

7. The method of claim 5, wherein the pH of the hypertonic saline solution is from 7.0 to 9.0.

8. The method of claim 7, wherein the hypertonic saline solution is administered to the subject as a nebulized solution.

9. The method of claim 8, wherein between 1 mL and 10 mL of hypertonic saline solution is administered to the subject.

10. The method of claim 3, wherein the subject has acute respiratory distress syndrome.

11. The method of claim 3, wherein the subject has a respiratory rate of 21-25 breaths/minute, a pulse rate of 91-110 beats/minute or has a NEWS2 Score of 0-4.

12. The method of claim 3, wherein the subject has a respiratory rate of 25-30 breaths/minute, a pulse rate of 111-130 beats/minute or has a NEWS2 Score of 5-6.

13. The method of claim 3, wherein the subject has a respiratory rate of 30-40 breaths/minute, the subject has a pulse rate of over 131 beats/minute or has a NEWS2 Score of 7 or greater.

14. The method of claim 3, wherein the subject has at least one risk factor for acute respiratory distress.

15. The method of claim 1, wherein the subject has a blood pulse-oximetry oxygen saturation level of less than 95%.

16. The method of claim 1, wherein the subject has a blood pulse-oximetry oxygen saturation level of less than 92%.

17. The method of claim 1, wherein the subject has a respiratory rate in excess of the 25-30 breathes/minute.

18. The method of claim 1, wherein the subject has a respiratory rate in excess of 30 to 40 breaths/minute.

* * * * *